United States Patent [19]

Wiezer

[11] 4,223,148

[45] Sep. 16, 1980

[54] POLYALKYL-PIPERIDINE DIOLS AND PROCESS FOR THEIR PREPARATION

[75] Inventor: Hartmut Wiezer, Gersthofen, Fed. Rep. of Germany

[73] Assignee: Hoechst Aktiengesellschaft, Fed. Rep. of Germany

[21] Appl. No.: 70,805

[22] Filed: Aug. 29, 1979

[30] Foreign Application Priority Data

Sep. 2, 1978 [DE] Fed. Rep. of Germany ....... 2838364

[51] Int. Cl.² .................. C07D 471/10; C07D 211/12
[52] U.S. Cl. ........................................ 546/242; 546/16
[58] Field of Search .................................. 546/242, 16

[56] References Cited

U.S. PATENT DOCUMENTS 4,014,887  3/1977  Randell et al. ........................ 546/16

Primary Examiner—Henry R. Jiles
Assistant Examiner—Robert T. Bond

Attorney, Agent, or Firm—Connolly and Hutz

[57] ABSTRACT

The invention provides novel polyalkyl-piperidine diols of the formula

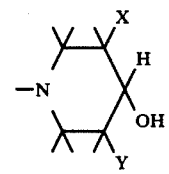

in which X≠Y and each stands for —H or —OH. They are prepared from the corresponding piperideines which are converted to the epoxides with organic peracids in an organic solvent, and subsequently the epoxide ring is split by addition of water. The products of the invention are suitable for the synthesis of polymer stabilizers for plastic materials.

5 Claims, No Drawings

POLYALKYL-PIPERIDINE DIOLS AND PROCESS FOR THEIR PREPARATION

The invention relates to novel polyalkyl-piperidine diols and a process for the preparation thereof.

The novel compounds correspond to the formula I

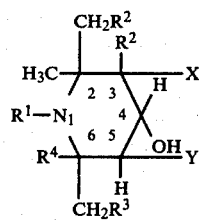

in which the substituents

X and Y are different and stand each for a hydroxyl group or a hydrogen atom;

$R^1$ is hydrogen, oxygen or $C_1$–$C_{12}$-alkyl, preferably hydrogen or $C_1$–$C_4$-alkyl, and especially hydrogen;

$R^2$ and $R^3$ are either identical and stand each for hydrogen or a $C_1$–$C_5$ alkyl group, and especially for hydrogen;

$R^4$ being a methyl group in this case; or $R^2$ is hydrogen or $C_1$–$C_5$-alkyl, and $R^3$ and $R^4$ together with the carbon atoms to which they are linked form a $C_5$-or $C_6$-cycloalkyl group, or a group of the formula

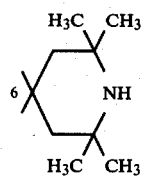

In the novel compounds, the ring nitrogen atom has basic properties when it is substituted by hydrogen or alkyl. In these cases, the compounds may also have the form of salts with inorganic or organic acids. Examples of such salts are phosphates, sulfates, chlorides, acetates, laurates, stearates, succinates, sebacates, maleates, citrates, tartrates, oxalates, benzoates, sulfonates, phosphonates, etc.

Individual examples of the novel polyalkyl-piperidine diols are the following:

2,2,6,6-Tetramethylpiperidine-3,4-diol;
1,2,2,6,6-Pentamethylpiperidine-3,4-diol;
1,9-Diaza-2,2,8,8,10,10-hexamethyl-spiro[5,5]-undecane3,4-diol;
1,9-Diaza-2,2,8,8,10,10-hexamethyl-spiro[5,5]-undecane4,5-diol;
2,3,6-Trimethyl-2,6-diethylpiperidine-3,4-diol;
2,3,6-Trimethyl-2,6-diethylpiperidine-4,5-diol;
2,2,6,6-Tetramethylpiperidine-3,4-diol-hydrochloride.

The novel compounds are obtained according to the following reaction scheme, in which the substitutents $R^1$ through $R^4$ are as defined above, by reacting polyalkyl-piperideines of the formulae (IIIa) and (IIIb) with peracids to form epoxides, and by adding water to the latter ones. The poly-piperideines for their part can be prepared from polyalkylpiperidin-4-oles (II) by splitting off water according to processes known from the literature or similar methods (see for example E. Fischer, Ber. 16, p. 1604; Ber. 17, p. 1790).

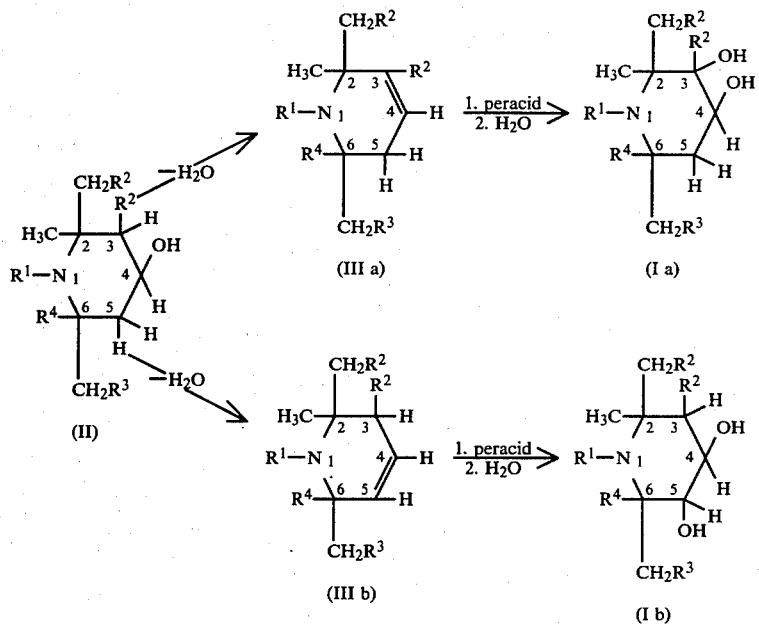

The dehydration of asymmetrically substituted polyalkyl-piperidin-4-oles (II) gives of course mixtures of polyalkyl-piperideines (IIIa) and (IIIb), and accordingly, mixtures of polyalkyl-piperidine diols (Ia) and (Ib) are formed in the further reaction.

For the preparation of polyalkyl-piperidine diols, either ready-to-use peracids or those formed in situ may be used as oxygen carrier. In the first case, operations are for example as follows: the polyalkyl-piperideine (III) in an inert organic solvent such as ether, dichloroethane, acetic acid or, preferably, formic acid is introduced into the reactor, and the equimolar to 1.2-fold molar amount, preferably the equimolar amount, of an organic peracid such as peracetic, perbenzoic or, especially, performic acid is added dropwise at 20°–40° C. in the form of a stable solution. Agitation is then continued for 2 to 20 hours, and the reaction mixture so obtained contains the epoxides, or the hydroxyformates of the epoxides in the case of using performic acid.

When the peracids are to be produced in situ, the polyalkyl-piperideine is added dropwise at 20°–70° C., preferably 20°–50° C., to a mixture of the 2- to 10-fold molar amount of the organic acid used as oxygen carrier, especially formic or acetic acid, and the equimolar to 1.2-fold molar, preferably 25 to 60 weight %, amount of hydrogen peroxide, relative to polyalkyl-piperideine (III), agitation is continued for 1 to 20 hours at about 20°–50° C. until the reaction is complete, and optionally, the batch is heated for 1 to 2 hours at 50°–60° C. in order to destroy excess peroxide.

The substantial amount of solvent is eliminated under reduced pressure from the reaction mixture obtained in the one or the other manner, the latter one is alkalized in cooled state with an aqueous alkaline solution, and subsequently heated for 2 to 20 hours at 60°–100° C. in order to split the epoxy ring by addition of water and to saponify esters possibly formed. Generally, an oily layer is thus formed which solidifies on cooling and which consists of the intended diols. The precipitated crystals are filtered off and purified by recrystallization, for example from a liquid hydrocarbon such as toluene or hexane.

The polyalkyl-piperidine diols where $R^1$ is alkyl can alternatively be prepared by posterior alkylation according to known methods of products where $R^1$ is H; the N-oxides can be synthetized from the compounds where $R^1$ is H by oxidation, for example with $H_2O_2$, in the presence of tungstate.

It was surprising and not to be expected that epoxidizing aliphatic and cycloaliphatic olefins with subsequent addition of water to form the diols, which process is known per se (see Houben-Weyl, vol. VI/3, pp. 371–487 (1965); Org. Reactions vol. 7, pp. 378–433 (1953)) succeeds in this special case, since formation of undesirable by-products had to be reckoned on. The polyalkyl-piperideines (III) used as starting materials for the synthesis of the novel polyalkyl-piperidine diols (I) have the olefin structure and the amino structure, too, as is well known, so that a side reaction (especially when $R^1$ is H) at the nitrogen atom of the piperideines, that is, formation of N-oxides according to the known oxidation of amines to N-oxides could not be excluded (see E. G. Rozantsev and V. D. Sholle, Synthesis 1971, pp. 190–202 and 401–414). A uniform course of the reaction would have been expected only in the case where compounds of the formula (II) where $R^1$ is O were used as starting material. Therefore, it was not to be expected at all that the polyalkyl-piperideines (III) can be converted nearly exclusively to the epoxides with the use of peracids, especially performic acid, even in the case where $R^1$ is hydrogen, and that there is no formation of N-oxides.

The novel polyalkyl-piperidine diols are suitable as light stabilizers for synthetic polymers. However, due to their bifunctionality, they are applied above all as starting material in the synthesis of high-quality polymeric stabilizers for plastics compositions.

The following examples illustrate the invention.

EXAMPLE 1

2,2,6,6-Tetramethyl-piperidine-3,4-diol 38 g of 2,2,6,6-tetramethyl-3-piperideine are added dropwise to a solution of 200 g of 98 to 100% formic acid and 30 g of 30% $H_2O_2$ within 1 hour ½. During this operation, the temperature rises to about 65° C., which temperature is maintained at 60°–65° C. by external cooling. After termination of the main reaction, agitation is continued for a further 16 hours, subsequently the batch is heated for 2 hours at 60° C., and then concentrated under reduced pressure to about 80 ml. Thereafter, it is alkalized with cooling with about 200 ml of 25% NaOH, agitated for 16 hours at 80° C., and the crystallized layer which forms a distinct phase after cooling is suction-filtered. 20 g of the intended diol are obtained in the form of the hydrate having a melting point of 105°–107° C. The free base having a m.p. of 139°–140° C. is obtained by recrystallization from toluene. The hydrochloride having a m.p. of 252° C. can be prepared by dissolving the free base for example in ether, and by treating this solution with gaseous hydrogen chloride.

EXAMPLE 2

The compound of Example 1 can be obtained alternatively in the following manner:

13.9 g (0.1 mol) of 2,2,6,6-tetramethyl-3-piperideine in 100 ml of 98 to 100% formic acid and 10 g of water are introduced into the reaction vessel. 19 g of 40% peracetic acid are added dropwise, the batch is carefully heated to 50°–55° C., and agitation is continued at this temperature for 24 hours. Subsequently, the batch is worked up as indicated in Example 1 (before concentration, a peroxide sample has to be negative). 10 g of white crystals are obtained which, recrystallized from toluene, have a melting point of 138°–140° C.

EXAMPLE 3

1-Methyl-2,2,6,6-tetramethyl-piperidine-3,4-diol 50 g of 1-methyl-2,2,6,6-tetramethyl-3-piperideine are added dropwise within 1.5 hours to a solution of 230 g of 98 to 100% formic acid and 50 g of 30% $H_2O_2$. The temperature rises to 65° C. in this operation, and it is maintained at 60°–65° C. by cooling. The following operations are as indicated in Example 1. A layer of petroleum ether is placed over the separating oil, thus causing the intended diol to crystallize slowly. 15 g of crystals are obtained which, recrystallized from hexane, have a melting point of 78° C.

EXAMPLE 4

The compound of Example 3 may be prepared alternatively in the following manner:

10 g of 98 to 100% formic acid and 10 g of 30% formaldehyde are added to 3 g of the 2,2,6,6-tetramethyl-piperidine-3,4-diol obtained according to Example 1 or 2. The batch is heated for 10 hours at about 100° C., and subsequently concentrated under reduced pressure to about 7 ml. The residue is alkalized with 20 ml of 25% NaOH, thus causing an oil to separate. After having placed a layer of petroleum ether over the oil phase, crystals are obtained which are recrystallized from hexane. 27.9 g; mp 78° C.

What is claimed is:

1. A polyalkyl-piperidine diol of the formula

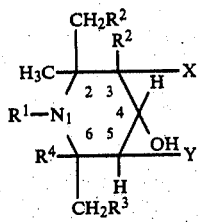
(I), in which
X and Y are different and stand each for a hydroxyl group or a hydrogen atom;
$R^1$ is hydrogen, oxygen or $C_1$-$C_{12}$-alkyl,
$R^2$ and $R^3$ are either identical and stand each for hydrogen or a $C_1$-$C_5$ alkyl group,
$R^4$ being a methyl group in this case; or
$R^2$ is hydrogen or $C_1$-$C_5$-alkyl, and
$R^3$ and $R^4$ together with the carbon atoms to which they are linked form a $C_5$-or $C_6$-cycloalkyl group, or a group of the formula

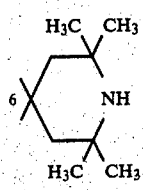

2. A compound as claimed in claim 1, in which $R^1$ is hydrogen or methyl, $R^2$ and $R^3$ are hydrogen, and $^4$ is methyl.

3. A process for the preparation of a compound as claimed in claim 1, which comprises epoxydizing a compound of the formulae (IIIa) or (IIIb)

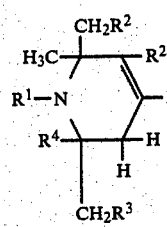
(III a)

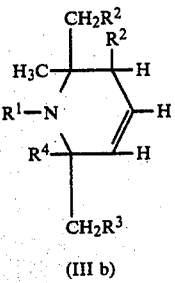
(III b)

in which $R^1$ through $R^4$ are as defined in claim 1, in the presence of an organic solvent and at temperatures of from 20° to 70° C. with either an organic peracid, or an organic acid acting as oxygen carrier and $H_2O_2$, and subsequently converting the epoxides formed or their acid addition products to the intended diols by addition of water or by saponification.

4. The process as claimed in claim 3, which comprises epoxidizing with the use of peracids, either preliminarily prepared or prepared in situ, in acetic or formic acid.

5. The process as claimed in claim 3, which comprises epoxidizing with the use of performic acid, either preliminarily prepared or prepared in situ, in formic acid as solvent.

* * * * *